United States Patent [19]

Bezwada

[11] 4,284,536

[45] Aug. 18, 1981

[54] COMPOSITION FOR ADHESION OF RUBBER TO REINFORCING MATERIALS

[75] Inventor: Rao S. Bezwada, Somerville, N.J.

[73] Assignee: American Cyanamid Co., Stamford, Conn.

[21] Appl. No.: 161,954

[22] Filed: Jun. 23, 1980

[51] Int. Cl.$^3$ ............................ C08L 7/00; C08L 9/00; C08L 9/06; C08L 61/24
[52] U.S. Cl. ..................................... 260/4 AR; 260/3; 260/4 R; 260/5; 525/160; 525/164; 548/318; 548/319
[58] Field of Search ................... 260/3, 4 R, 4 AR, 5; 525/347, 341, 160, 164; 548/318, 319

[56] References Cited

U.S. PATENT DOCUMENTS

| | | | |
|---|---|---|---|
| 3,369,004 | 2/1968 | Stanton | 525/347 |
| 3,517,722 | 6/1970 | Endter et al. | 260/3 |
| 3,553,115 | 1/1971 | Curchod et al. | 525/164 |
| 3,652,583 | 3/1972 | Tajima et al. | 548/319 |
| 3,715,172 | 2/1973 | Dembowski et al. | 525/164 |
| 3,778,406 | 12/1973 | Klötzer et al. | 260/3 |
| 3,926,703 | 12/1975 | Cantor | 260/3 |
| 3,951,887 | 4/1976 | Tanimura et al. | 260/3 |
| 3,992,334 | 11/1976 | Harvey | 260/3 |
| 4,014,827 | 3/1977 | Hart et al. | 260/3 |

*Primary Examiner*—Allan Lieberman
*Attorney, Agent, or Firm*—Frank M. Van Riet

[57] ABSTRACT

A vulcanizable rubber composition comprising a rubber, a vulcanizing agent and various imidazolidinones is disclosed.

10 Claims, No Drawings

COMPOSITION FOR ADHESION OF RUBBER TO REINFORCING MATERIALS

BACKGROUND OF THE INVENTION

It has been conventional practice to prepare various textile reinforcing fibers, to be used in contact with rubber compositions, by pretreating them with a rubber latex and a phenol-formaldehyde resin in which the phenol has almost always been resorcinol. This is the so-called "RFL" (Resorcinol-Formaldehyde-Latex) method. Another method commonly used is to generate the resin in situ in the vulcanized rubber-textile matrix by incorporating therein a formaldehyde (or methylene) donor compound, for example, hexamethylenetetramine or hexamethoxymethylmelamine, and a formaldehyde (or methylene) acceptor compound, for example, resorcinol. This method has been particularly effective where the reinforcing material is brass-coated steel wire, since pretreatment of the wire by the aforementioned "RFL" method has proven to be largely ineffective. The methylene donor-acceptor method is described by Endter, U.S. Pat. No. 3,517,722.

SUMMARY OF THE INVENTION

It has now been found that excellent adhesion of rubber to reinforcing materials, such as textile fibers or brass-coated steel wire, is achieved by the incorporation into the rubber composition, before vulcanization thereof in the presence of reinforcing materials, of a compound selected from those of Formula I, II or III, below.

Such materials have not been used heretofore in the adhesion of textile fibers or steel wire to rubber. It is quite surprising that excellent adhesion, usually equal to or better than that which is attained by existing compositions, is achieved by the use of the compounds alone, since it would appear to deviate from the commonly accepted methylene donor-acceptor theory of adhesion to do so.

DESCRIPTION OF THE INVENTION

The novel vulcanizable compositions of the instant invention consist essentially of (A) natural or synthetic rubber or a mixture thereof, (B) a vulcanizing agent and (C) a compound represented by Formula I, II or III, more fully defined immediately hereinbelow.

The compounds constituting component (C) of the novel compositions hereof have the following structural formulae:

$$\text{ROCH}_2-\text{N} \underset{\text{HO} \quad \text{OH}}{\overset{\overset{\displaystyle O}{\overset{\|}{C}}}{\diagdown}} \text{N}-\text{CH}_2\text{OR}' \quad \text{(I)}$$

$$R^2-\text{N} \underset{\text{HO} \quad \text{OH}}{\overset{\overset{\displaystyle O}{\overset{\|}{C}}}{\diagdown}} \text{N}-R^3 \quad \text{(II)}$$

$$R^4O+CH_2)_{\overline{n}}\left[-N\underset{\text{HO} \quad \text{OH}}{\overset{\overset{\displaystyle O}{\overset{\|}{C}}}{\diagdown}}N-CH_2\right]_x -N\underset{\text{HO} \quad \text{OH}}{\overset{\overset{\displaystyle O}{\overset{\|}{C}}}{\diagdown}}N-(CH_2)_n OR^5 \quad \text{(III)}$$

In the above formulae, R and R' are, individually, lower ($C_1$-$C_4$) alkyl, aryl ($C_6$-$C_{10}$) or cycloalkyl wherein the ring contains 5 or 6 carbon atoms; $R^2$ and $R^3$ are, individually, alkyl ($C_1$-$C_8$), aryl, ($C_6$-$C_{10}$), cycloalkyl wherein the ring contains 5 or 6 carbon atoms, cyano, carboxy, carbalkoxy, or amido or dialkylamido substituted lower ($C_1$-$C_4$) alkyl or hydroxy substituted lower ($C_2$-$C_4$) alkyl; $R^4$ and $R^5$ are, individually, hydrogen, lower ($C_1$-$C_4$) alkyl, or cycloalkyl wherein the ring contains 5 or 6 carbon atoms; n is an integer from 1-4 inclusive, and x is 1 to 2.

The compounds represented by Formulae I, II & III, are readily prepared by the reaction of urea, or a substituted urea, glyoxal, formaldehyde, and an alcohol. Compounds of Formula I are obtained by reaction of about one molar proportion of urea, about one molar proportion of glyoxal, about 2 molar proportions of formaldehyde, and about 2 molar proportions of a lower alkanol, a phenol, or a cycloalkanol. Such compounds include:

1,3-dimethoxymethyl-4,5-dihydroxyimidazolidinone;
1,3-diethoxymethyl-4,5-dihydroxyimidazolidinone;
1,3-dibutoxymethyl-4,5-dihydroxyimidazolidinone;
1,3-diphenoxymethyl-4,5-dihydroxyimidazolidinone;
1,3-dicyclohexyloxymethyl-4,5-dihydroxyimidazolidinone, and the like.

Compounds of Formula II are prepared most readily by the reaction of about one molar proportion of a disubstituted urea compound with about one molar proportion of glyoxal. Such compounds include:

1,3-dimethyl-4,5-dihydroxyimidazolidinone;
1,3-diethyl-4,5-dihydroxyimidazolidinone;
1,3-dibutyl-4,5-dihydroxyimidazolidinone;
1,3-dioctyl-4,5-dihydroxyimidazolidinone;
1,3-diphenyl-4,5-dihydroxyimidazolidinone;
1,3-di(β-naphthyl)-4,5-dihydroxyimidazolidinone;
1,3-dicyclohexyl-4,5-dihydroxyimidazolidinone;
1,3-di(2-hydroxyethyl)-4,5-dihydroxyimidazolidinone;
1,3-di(2-cyanoethyl)-4,5-dihydroxyimidazolidinone;
1,3-di(2-carboxyethyl)-4,5-dihydroxyimidazolidinone;
1,3-di(2-carbomethoxyethyl)-4,5-dihydroxyimidazolidinone;
1,3-di(cyanomethyl)-4,5-dihydroxyimidazolidinone,
1,3-di(hydroxypropyl)-4,5-dihydroxyimidazolidinone;
1,3-di(cyanobutyl)-4,5-dihydroxyimidazolidinone;
1,3-di(amidomethyl)-4,5-dihydroxyimidazolidinone;
1,3-di(N,N-dimethylamidoethyl)-4,5-dihydroxyimidazolidinone, and the like.

Compounds of Formula III are prepared, depending on whether x is 1 or 2, as follows: When x is 1, about one molar proportion of a methylenebis (substituted urea) is reacted with about two molar proportions of glyoxal. The methylenebis (substituted) has the formula IV.

$$\text{HO} + \text{CH}_2)_{\overline{n}}\text{NH}-\overset{\overset{\displaystyle O}{\|}}{\text{C}}-\text{NH}-\text{CH}_2-\text{NH}-\overset{\overset{\displaystyle O}{\|}}{\text{C}}-\text{NH}+\text{CH}_2)_{\overline{n}}\text{OH} \quad \text{(IV)}$$

This methylenebis (substituted urea) is then reacted with the glyoxal and the resultant hydroxyalkyl product can then optionally be etherified with an appropriate $C_1$–$C_4$ alkane or a cycloalkanol to produce the product wherein $R^4$ and $R^5$ are alkyl or cycloalkyl.

When x is 2, about 2 molar proportions of a monosubstituted urea, about one molar proportion of urea, about 2 molar proportions of formaldehyde, and about 2 molar proportions of glyoxal are reacted. The monosubstituted urea has the formula:

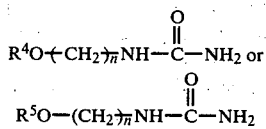

where $R^4$, $R^5$, and n are as defined above. In all instances, $R^4$ and $R^5$ may be the same or different. Preferably, $R^4$ and $R^5$ are the same.

Such compounds include, where x=1:
1,1'-methylenebis[3-(2-hydroxyethyl)-4,5-dihydroxyimidazolidinone];
1,1'-methylenebis[3-methoxyethyl-4,5-dihydroxyimidazolidinone];
1,1'-methylenebis[3-ethoxypropyl-4,5-dihydroxyimidazolidinone];
1,1'-methylenebis[3-cyclohexyloxyethyl-4,5-dihydroxyimidazolidinone];
1,1'-methylenebis[3-(3-hydroxypropyl)-4,5-dihydroxyimidazolidinone];
1,1'-methylenebis[3-(4-hydroxybutyl)-4,5-dihydroxyimidazolidinone];
1,1'-methylenebis[3-8 butoxymethyl-4,5-dihydroxyimidazolidinone] and the like.

Where x is 2:
4,5-dihydroxy-1,3-bis[4,5-dihydroxy-3-hydroxyethyl-2-oxo-1-imidazolidinyl]-methyl-2-imidazolidinone;
4,5-dihydroxy-1,3-bis[4,5-dihydroxy-3-hydroxybutyl-2-oxo-1-imidazolidinyl]-methyl-2-imidazolidinone;
4,5-dihydroxy-1,3-bis[4,5-dihydroxy-3-methoxymethyl-2-oxo-1-imidazolidinyl]-methyl-2-imidazolidinone;
4,5-dihydroxy-1,3-bis[4,5-dihydroxy-3-methoxypropyl-2-oxo-1-imidazolidinyl]-methyl-2-imidazolidinone;
4,5-dihydroxy-1,3-bis[4,5-dihydroxy-3-butoxyethyl-2-oxo-1-imidazolidinyl]-methyl-2-imidazolidinone;
4,5-dihydroxy-1,3-bis[4,5-dihydroxy-3-methoxybutyl-2-oxo-1-imidazolidinyl]-methyl-2-imidazolidinone;
4,5-dihydroxy-1,3-bis[4,5-dihydroxy-3-cyclohexyloxyethyl-2-oxo-1-imidazolidinyl]-methyl-2-imidazolidinone, and the like.

The improved vulcanizable compositions of the present invention may be used in bonding reinforcing fibers or wire to rubber used in the manufacture of tires, drive belts, conveyor belts, pressure hoses, and the like. The rubber used may be natural rubber; synthetic diene rubbers, such as polybutadiene, polyisoprene; ethylene propylene terpolymer rubber (EPDM); butadiene-styrene rubber (SBR); butadiene acrylonitrile rubber (NBR); chloroprene rubber; chlorosulfonated polyethylene; and mixtures thereof.

The reinforcing materials useful herein include textile materials, in the form of fibers or fabrics, commonly used to reinforce rubber compositions, which includes cotton, rayon, polyamides, polyesters, polyimides, and the like, and metallic materials, such as wires and cord threads of raw steel, brass-coated steel, and the like. The invention is particularly useful with brass-coated steel wire.

The vulcanizable rubber composition to which the reinforcing materials are bonded during vulcanization contain, in addition to the promoter compound, the vulcanizing agent and the rubber, other conventional compounding ingredients such as carbon black, antioxidants, sulfur, accelerators, zinc oxide, high surface area silica (including mixtures thereof with carbon black), processing and softening oils, and the like.

The promoter compounds of the composition of the invention, as represented by Formulae I, II and III, above, are incorporated into the vulcanizable rubber composition in an amount of from about 1 to 10 parts by weight per hundred parts by weight of rubber used. Preferably, the compounds are used in an amount of from about 2 to 4 parts by weight, same basis.

For optimum adhesion of the reinforcing material to rubber, particularly using brass-coated steel wire, it has been found desirable to incorporate into the rubber composition a high surface area silica. The reason for enhanced adhesion in the presence of high surface area silica is speculative, but may result from hydrogen bonding of hydroxyl groups of the silica with the components of the vulcanization system. The silica is used in an amount of from about 2 to 14 parts by weight per hundred parts of rubber, preferably about 8 to 12 parts by weight, same basis, although good adhesion is still obtained in the absence of silica.

Adhesion is measured using ASTM D-2229-73 with 15-reinforcing members embedded in a $0.5'' \times 0.5'' \times 8''$ block of rubber. The force to pull the metal cord or textile fiber out of the rubber is recorded in pounds per linear inch (pli) of embedded length.

The following examples are provided by way of further illustration of the particular features of the invention. All parts are by weight unless otherwise specified.

EXAMPLE A 1,1'-Methylenebis(3-hydroxymethyl-4,5-dihydroxyimidazolidin-2-one)

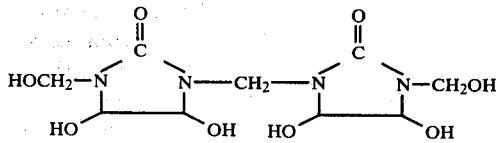

Glyoxal (1.0 mole, 145 parts of 40% aqueous solution) and formaldehyde (1.5 moles, 126 parts of 37% aqueous solution) are charged to a suitable reaction vessel and the pH is adjusted to about 7 with sodium bicarbonate. Urea (1.0 mole, 60 parts) is added at room temperature, allowing the temperature to rise to about 45° C. When the temperature subsides to about room temperature, the mixture is stirred at room temperature for about 16 hours and then heated at about 50° C. at a pH of about 7–7.5 until the free formaldehyde content is essentially zero. After 7 hours, the formaldehyde content is 0.16%. The titled compound is recovered in good yield.

EXAMPLE B 1,1'-Methylenebis(3-methoxymethyl-4,5-dihydroxyimidazolidin-2-one)

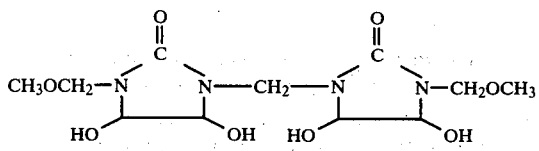

The product of Example 1 (163 parts) is mixed with 68 parts of methanol. The pH is adjusted to 1.5–2 with concentrated nitric acid and the mixture is heated at 60° C. for about 3 hours. The pH is again adjusted to about 6 with sodium hydroxide, the reaction mixture is cooled to room temperature and excess methanol is stripped off in vacuo to leave the titled compound in good yield.

EXAMPLE C–G

The following compounds are similarly prepared: (C) 1,1'-methylenebis(3-ethoxymethyl-4,5-dihydroxyimidazolidin-2-one) (from ethanol); (D) 1,1'-methylenebis(3-propoxymethyl-4,5-dihydroxyimidazolidin-2-one) (from propanol); (E) 1,1'-methylenebis(3-butoxymethyl-4,5-dihydroxyimidazolidin-2-one) (from butanol); (F) 1,1'-methylenebis(3-phenoxymethyl-4,5-dihydroxyimidazolidin-2-one) (from phenol; (G) 1,1'-methylenebis(3-cyclohexyloxymethyl-4,5-dihydroxyimidazolidin-2-one) (from cyclohexanol).

EXAMPLE H 1,1'-Methylenebis[3-(2-hydroxyethyl)-4,5-dihydroxyimidazolidin-2-one]

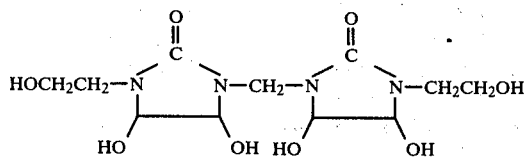

Methylenebis(2-hydroxyethylurea), 754 parts, and 754 parts of water are mixed and 894.2 parts of 40% glyoxal are added. The mixture is heated to 60° C. and stirred for 30 minutes. The pH is adjusted to 6–7 and the mixture stirred at 55° C. for one hour. Residual glyoxal is 1.37%. Additional methylenebis(2-hydroxyethylurea), 60 parts, is added and heating continued for 0.5 hour at 60° C. The compound is obtained as a 50% solution in water in high yield.

EXAMPLES I–N

The following compounds are similarly prepared:
(I) 1,1'-methylenebis[3-(4-methoxybutyl)-4,5-dihydroxyimidazolidin-2-one];
(J) 1,1'-methylenebis[3-(2-methoxyethyl)-4,5-dihydroxyimidazolidin-2-one];
(K) 1,1'-methylenebis[3-(cyclohexyloxyethyl)-3,5-dihydroxyimidazolidin-2-one];
(L) 1,1'-methylenebis[4-butoxybutyl)-4,5-dihydroxyimidazolidin-2-one];
(M) 1,1'-methylenebis[3-hydroxybutyl-4,5-dihydroxyimidazolidin-2-one];
(N) 1,1'-methylenebis[3-methoxypropyl-4,5-dihydroxyimidazolidin-2-one];
from methylenebis(4-methoxybutylurea), methylenebis(2-methoxyethylurea), methylenebis(2-cyclohexyloxyethyl)urea, methylenebis-4-butoxybutyl)urea, methylenebis(hydroxybutylurea), methylenebis(3-methoxypropylurea), respectively.

EXAMPLE O 4,5-Dihydroxy-1,3-bis[4,5-dihydroxy-3-(2-hydroxyethyl)-2-oxo-1-imidazolidinyl]-methyl-2-imidazolidinone

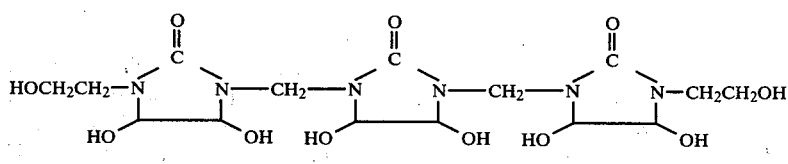

1-(2-Hydroxyethylurea), 60 parts, is mixed with 46.5 parts of formaldehyde. The pH is adjusted to 2–3 and the mixture heated at 50°–60° C. for one hour. Then, 18 parts of urea are added, the pH adjusted to 2, and the mixture heated at 60° C. When a white milky material begins to form, 83.6 parts of glyoxal are added and the mixture heated at 90° C. for 0.5 hour. A clear, pale yellow solution forms, to which an additional 20 parts of glyoxal are added, and heating is continued at 80°–90° C. for about 30 minutes. The mixture is conneutralized to obtain a 50% aqueous solution of product in good yield.

EXAMPLES P–S

Following a similar procedure, the following compounds are prepared: (P) 4,5-dihydroxy-1,3-bis[4,5-dihydroxy-3-methoxyethyl-2-oxo-1-imidazolidinyl]-methyl-2-imidazolidinone (from 1-methoxyethylurea); (Q) 4,5-dihydroxy-1,3-bis-[4,5-dihydroxy-3-methoxybutyl-2-oxo-1-imidazolidinyl]-methyl-2-imidazolidinone (from 1-methoxybutylurea); (R) 4,5-dihydroxy-1,3-bis[4,5-dihydroxy-3-cyclohexyloxyethyl-2-oxo-1-imidazolidinyl]-methyl-2-imidazolidinone (from 1-cyclohexyloxyethylurea); (S) 4,5-dihydroxy-1,3-bis[4,5-dihydroxy-3-butoxybutyl-2-oxo-1-imidazolidinyl]-methyl-2-imidazolidinone (from 1-butoxybutylurea).

EXAMPLE T 4,5-Dihydroxy-1,3-dimethyl-2-imidazolidinone

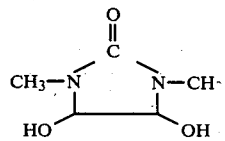

Dimethylurea (2-moles, 176 parts) and glyoxal (2 moles, 290 parts of 40% aqueous solution) are mixed and the pH adjusted to 7 with sodium hydroxide. The reaction mixture is stirred at room temperature for several hours and the resulting white solid is filtered, washed with methanol and dried. White crystals, melting point 140° C. are obtained in fine yield.

EXAMPLES U–A³

The following compounds are similarly prepared:
(U) 4,5-dihydroxy-1,3-diethyl-2-imidazolidinone
(V) 4,5-dihydroxy-1,3-dibutyl-2-imidazolidinone
(W) 4,5-dihydroxy-1,3-dioctyl-2-imidazolidinone
(X) 4,5-dihydroxy-1,3-dicyclohexyl-2-imidazolidinone
(Y) 4,5-dihydroxy-1,3-diphenyl-2-imidazolidinone
(Z) 4,5-dihydroxy-1,3-di(2-hydroxyethyl)-2-imidazolidinone
(A¹) 4,5-dihydroxy-1,3-di(2-cyanoethyl)-2-imidazolidinone
(A²) 4,5-dihydroxy-1,3-di(carboxybutyl)-2-imidazolidinone
(A³) 4,5-dihydroxy-1,3-di(carbomethoxyethyl)-2-imidazolidinone, each being prepared from the corresponding disubstituted urea.

EXAMPLE A⁴

An aqueous solution containing 45 percent, by weight, of 1,3-dimethylol-4,5-dihydroxy-2-imidazolidinone, prepared in accordance with the procedure of Example 1 of U.S. Pat. No. 3,903,033 to Chao, is evaporated to give a 90% solution thereof and is then contacted with methanol at a pH of 2–4 at 60° C. for about 2–3 hours. After adjustment of the pH to about 6, the reaction media is cooled to room temperature, excess methanol is stripped off and the resultant methylether of the charge compound is recovered.

EXAMPLES A⁵–A⁷

The corresponding di-n-octylether (A⁵), diphenylether (A⁶) and dicyclopentylether (A⁷) are prepared from the corresponding alcohols, i.e., octanol, phenol and cyclopentanol, respectively, with suitable pH adjustments.

A polyblend of natural rubber, polybutadiene and styrene-butadiene (25/75) rubber is compounded as follows and used in the evaluation of the compositions of the invention:

| Polyblend Masterbatch Formulation A | |
|---|---|
| | Parts by Weight |
| Natural rubber | 52 |
| Polybutadiene rubber | 18 |
| Styrene/butadiene rubber | 30 |
| Carbon black | 40 |
| Zinc Oxide | 5 |
| Stearic acid | 2 |
| Antioxidant⁽¹⁾ | 2 |
| High surface area silica | 10 |

⁽¹⁾Reaction product of diphenylamine and acetone; 50% active

Similarly, a natural rubber masterbatch is formulated as follows:

| Natural Rubber Masterbatch Formulation B | |
|---|---|
| | Parts by Weight |
| Natural rubber | 100 |
| Carbon black | 40 |
| Zinc Oxide | 5 |
| Stearic acid | 2 |
| Antioxidant⁽¹⁾ | |
| High surface area silica | 10 |

⁽¹⁾Reaction product of diphenylamine and acetone; 50% active

In the examples which follow, one or the other of the polyblend or natural rubber masterbatch formulation is used, in each case in an amount containing 100 parts rubber.

EXAMPLES 1–2

4,5-Dihydroxy-1,3-dimethyl-2-imidazolidinone (Example 1) and 4,5-dihydroxy-1,3-diethyl-2-imidazolidinone (Example 2) are evaluated as adhesion promoters in the polyblend masterbatch formulation as follows:

| Composition | Control | 1 | 2 |
|---|---|---|---|
| Masterbatch | 159.0 | 159.0 | 159.0 |
| Sulfur | 2.4 | 2.4 | 2.4 |
| Accelerator⁽²⁾ | 1.25 | 1.25 | 1.25 |
| Promoter | — | 3.0 | — |
| Promoter | — | — | 3.0 |

⁽²⁾N-oxydiethylene benzothiazole-2-sulfonamide

The compositions are compounded on a standard rubber mill for 10 minutes at 50°–80° C., embedded with 15 clean, brass-coated steel wires, placed parallel, and vulcanized at 153° C. Properties are given below.

| | Control | 1 | 2 |
|---|---|---|---|
| Stress Strain Properties | | | |
| Modulus @ 100%, MPa* | 2.6 | 2.4 | 2.2 |
| Modulus @300%, MPa | 12.9 | 11.2 | 10.5 |
| Tensile, MPa | 21.0 | 21.4 | 22.1 |
| Elongation, % | 421 | 468 | 488 |
| Hardness, Shore A | 62 | 62 | 61 |
| Adhesion Properties, kN/m** | | | |
| Unaged | 32.4 | 37.3 | 35.0 |

*1 MPa = 145.038 psi
**1 kN/m = 5.71 pli

EXAMPLES 3–6

1,1'-Methylenebis(3-hydroxymethyl-4,5-dihydroxyimidazolidin-2-one) (Example 3); 1,1'-methylenebis(3-methoxymethyl-4,5-dihydroxyimidazolidin-2-one) (Example 4); 1,1'-methylenebis[3-(2-hydroxyethyl)-4,5-dihydroxyimidazolidin-2-one] (Example 5); and 4,5-dihydroxy-1,3-di(methoxymethyl)-2-imidazolidinone (Example 6) are evaluated as adhesion promoters in natural rubber, as follows:

| | Control | 3 | 4 | 5 | 6 |
|---|---|---|---|---|---|
| Natural Rubber Masterbatch | 317 | 317 | 317 | 317 | 317 |
| Sulfur | 7.5 | 7.5 | 7.5 | 7.5 | 7.5 |
| Accelerator | 1.6 | 1.6 | 1.6 | 1.6 | 1.6 |
| Promoter | — | 6 | — | — | — |
| Promoter | — | — | 6 | — | — |
| Promoter*** | — | — | — | 11.5 | — |
| Promoter | — | — | — | — | 6 |

***52.4% solution

The compositions are compounded on a standard rubber mill for 10 minutes at 50°–80° C., embedded with 15 clean, brass-coated steel wires, placed parallel, and vulcanized at 153° C. Properties are given below.

|  | Control | 3 | 4 | 5 | 6 |
|---|---|---|---|---|---|
| Stress-Strain Properties |  |  |  |  |  |
| Modulus @ 100%, MPa | 2.58 | 2.6 | 2.5 | 2.4 |  |
| Modulus @ 300%, MPa | 13.7 | 12.2 | 12.0 | 12.3 | 11.9 |
| Tensile, MPa | 26.3 | 24.5 | 25.2 | 25.7 | 25.6 |
| Elongation, % | 485 | 495 | 504 | 509 | 517 |
| Hardness, Shore A | 62 | 65 | 63 | 62 | 63 |
| Adhesion Properties, kN/m |  |  |  |  |  |
| Unaged | 29.5 | 44.3 | 38.2 | 39.8 | 42.4 |
| Aged 4 days/85° C./100% RH | 23.0 | 30.4 | 28.4 | 25.7 | 31.7 |

EXAMPLES 7–35

The procedure of Example 1 is again followed except that a different promoter compound is employed in each instance and the masterbatch is varied. The various compositions are set forth in Table I, below. In each instance, substantially equivalent results are observed.

TABLE I

| Example | Promoter of Example No. | Masterbatch |
|---|---|---|
| 7 | C | A |
| 8 | D | A |
| 9 | E | A |
| 10 | F | B |
| 11 | G | A |
| 12 | I | B |
| 13 | J | B |
| 14 | K | B |
| 15 | L | A |
| 16 | M | B |
| 17 | N | B |
| 18 | O | A |
| 19 | P | B |
| 20 | Q | A |
| 21 | R | B |
| 22 | S | B |
| 23 | U | B |
| 24 | V | A |
| 25 | W | A |
| 26 | X | A |
| 27 | Y | A |
| 28 | Z | A |
| 29 | $A^1$ | A |
| 30 | $A^2$ | B |
| 31 | $A^3$ | A |
| 32 | $A^4$ | B |
| 33 | $A^5$ | B |
| 34 | $A^6$ | B |
| 35 | $A^7$ | A |

I claim:

1. A vulcanizable rubber composition consisting essentially of (A) a rubber comprising natural rubber, polybutadiene, polyisoprene, ethylenepropylene terpolymer rubber, butadiene-styrene copolymer rubber, butadiene-acrylonitrile copolymer rubber, chloroprene rubber, chlorosulfonated polyethylene or a mixture thereof; (B) a sulfur vulcanizing agent; and (C) from about 1 to 10 parts by weight, per hundred parts by weight of rubber, of a compound selected from the group consisting of (1) compounds of the formula:

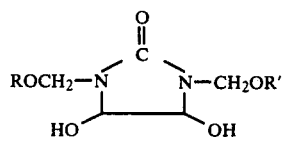

wherein R and R' are individually lower ($C_1$–$C_4$) alkyl, aryl ($C_6$–$C_{10}$) or cycloalkyl having 5 or 6 carbon atoms in the ring; (2) compounds of the formula:

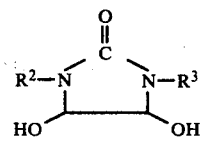

wherein $R^2$ and $R^3$ are individually alkyl ($C_1$–$C_8$) aryl ($C_6$–$C_{10}$), cycloalkyl having 5 or 6 carbon atoms in the ring, cyano, carboxy, carboalkoxy, amido or dialkylamido substituted lower ($C_1$–$C_4$) alkyl or hydroxy substituted lower ($C_2$–$C_4$) alkyl; or (3) compounds of the formula:

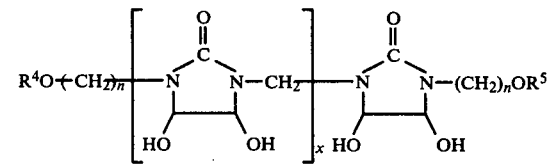

wherein $R^4$ and $R^5$ are, individually, hydrogen, lower ($C_1$–$C_4$) alkyl, or cycloalkyl having 5 or 6 carbon atoms in the ring; n is an integer from 1 to 4, inclusive, and x is 1 or 2.

2. A composition according to claim 1 wherein the rubber is natural rubber.

3. A composition according to claim 1 wherein component (C) has the formula:

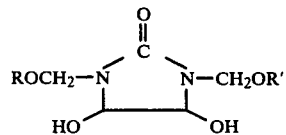

wherein R and $R^1$ are, individually, lower ($C_1$–$C_4$) alkyl, aryl ($C_6$–$C_{10}$) or cycloalkyl having 5 or 6 carbon atoms in the ring.

4. A composition according to claim 1 wherein component (C) has the formula:

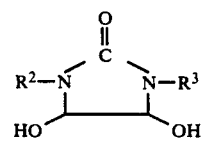

wherein $R^2$ and $R^3$ are, individually, alkyl ($C_1$–$C_8$), aryl ($C_6$–$C_{10}$), cycloalkyl having 5 or 6 carbon atoms in the ring, hydroxy substituted lower alkyl ($C_2$–$C_4$) or cyano, carboxy, carboalkoxy, amido or dialkylamido substituted lower alkyl ($C_1$–$C_4$).

5. A composition according to claim 1 wherein component (C) has the formula:

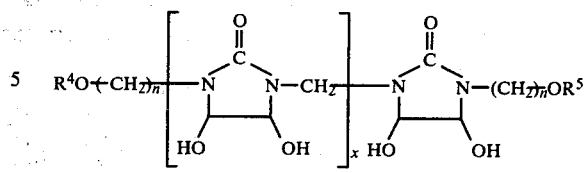

wherein $R^4$ and $R^5$ are, individually, hydrogen, lower ($C_1$–$C_4$) alkyl or cycloalkyl having 5 or 6 carbon atoms in the ring, n is an integer from 1–4, inclusive, and n is 1 or 2.

6. A composition according to claim 3 wherein R and $R^1$ are methyl.

7. A composition according to claim 4 wherein $R^2$ and $R^3$ are methyl.

8. A composition according to claim 5 wherein n is 1, $R^4$ and $R^5$ are methyl and x is 1.

9. A composition according to claim 5 wherein n is 1, $R^4$ and $R^5$ are methyl and x is 2.

10. A composition according to claim 1 containing, additionally, D, from about 2 to 14 parts, by weight, per hundred parts of rubber, high surface area silica.

* * * * *